United States Patent
Sasaki

(10) Patent No.: US 6,423,042 B1
(45) Date of Patent: Jul. 23, 2002

(54) PANTS-TYPE DISPOSABLE DIAPER

(75) Inventor: Toru Sasaki, Kagawa-ken (JP)

(73) Assignee: Uni-Charm Corporation (JP)

( * ) Notice: Subject to any disclaimer, the term of this patent is extended or adjusted under 35 U.S.C. 154(b) by 0 days.

(21) Appl. No.: 09/300,805

(22) Filed: Apr. 27, 1999

(30) Foreign Application Priority Data

Apr. 28, 1998 (JP) .......................................... 10-118664

(51) Int. Cl.$^7$ ................................................. A61F 13/15
(52) U.S. Cl. ........................ 604/385.01; 604/385.02; 604/385.13; 604/358; 604/386; 128/290
(58) Field of Search ................. 604/385.01, 385.14, 604/385.03, 385.13, 385.02, 386, 378

(56) References Cited

U.S. PATENT DOCUMENTS

| | | | |
|---|---|---|---|
| 3,672,371 A | * 6/1972 | Roeder | ........................ 128/290 |
| 4,337,772 A | * 7/1982 | Roeder | .................... 128/290 R |
| 4,655,760 A | 4/1987 | Morman et al. | |
| 4,690,680 A | * 9/1987 | Higgins | ...................... 604/386 |
| 5,030,303 A | * 7/1991 | Cucuzza | .................. 604/385.02 |
| 5,171,302 A | * 12/1992 | Buell | ...................... 604/385.1 |
| 5,246,431 A | * 9/1993 | Minetola et al. | ......... 604/385.2 |
| 5,429,631 A | * 7/1995 | Grenier | ................. 604/385.01 |
| 5,454,802 A | 10/1995 | Lindquist et al. | |
| 5,683,374 A | 11/1997 | Yamamoto et al. | |
| 6,056,732 A | * 5/2000 | Fujioka | .................. 604/385.01 |
| 6,061,839 A | * 5/2000 | Smolik | ........................ 604/358 |
| 6,198,019 B1 | * 3/2001 | Hansson | ...................... 604/378 |
| 6,210,386 B1 | * 4/2001 | Inoue | .................... 604/385.13 |

FOREIGN PATENT DOCUMENTS

| | | | |
|---|---|---|---|
| EP | 0 735 850 | 10/1996 | |
| EP | 0761194 A2 | * 3/1997 | ................. 604/358 |
| EP | 0 804 914 | 11/1997 | |
| GB | 2 253 131 | 9/1992 | |
| GB | 2 262 873 | 7/1993 | |
| JP | 8-112308 | 5/1996 | |
| JP | 9-56746 | 3/1997 | |

* cited by examiner

*Primary Examiner*—John L. Calvert
*Assistant Examiner*—Angela G Grayson
(74) *Attorney, Agent, or Firm*—Baker & Daniels

(57) ABSTRACT

A disposable diaper includes a pants-type outer cover and a liquid-absorbent pad. The outer cover has a zone adapted to cover the wearer's urethral meatus and the area in the vicinity thereof and being elastic transversely of the diaper. The pad is attached to an inner surface of the outer cover and its zone intended to be placed against the urethral meatus and the area in the vicinity thereof is placed upon the corresponding zone of the outer cover adapted to cover the urethral meatus and the area in the vicinity thereof and then joined to the outer cover along two zones defined on the outer cover so as to be spaced apart from each other transversely of the diaper.

3 Claims, 4 Drawing Sheets

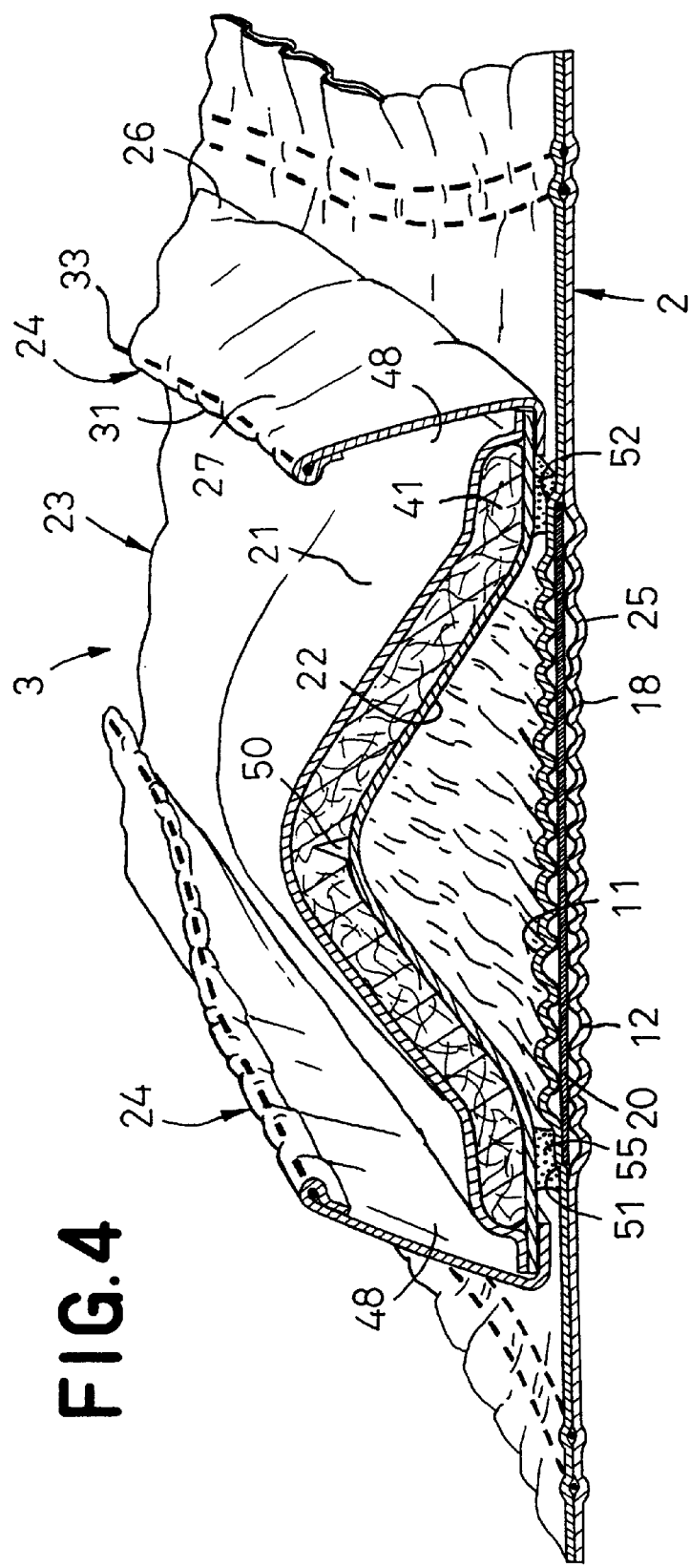

PANTS-TYPE DISPOSABLE DIAPER

BACKGROUND OF THE INVENTION

The present invention relates to a pants-type disposable diaper for absorbing and containing body exudates.

Japanese Patent Application Disclosure Gazette No. Hei8-112308 discloses a pants-type disposable diaper having elastic members extending across a zone corresponding to a wearer's body zone including the urethral meatus transversely of the diaper and secured to the diaper with appropriate tension. According to the disclosure, a fitting of the diaper to the body zone including the urethral meatus is improved by such an arrangement.

Japanese Patent Application Disclosure Gazette No. Hei9-56746 discloses a pants-type body fluids absorbent article comprising a pants-type outer cover and a liquid absorbent pad attached to an inner surface of the outer cover and extending across a crotch region into front and rear waist regions of the outer cover. The outer cover is provided in the vicinity of the uppermost points of respective leg-openings with elastic members circumferentially extending in the waist regions and the crotch region of the cover member is elastic longitudinally of the article.

The diaper disclosed in the Japanese Patent Application Disclosure Gazette No. Hei8-112308 is characterized by that a liquid-absorbent body comprising a liquid-absorbent core disposed between topsheet and the backsheet is provided with the elastic members extending transversely of the diaper. The elastic members serve to fit the waist regions of the diaper to the wearer's body and thereby to improve a fitting of the diaper also in the zone including the urethral meatus. However, such an improvement of the fitting relies on a circumferential fitting of the diaper and can not meet a requirement that the diaper should be pressed against the urethral meatus vertically or obliquely from below.

With the article disclosed in the Japanese Patent Application Disclosure Gazette No. Hei9-56746, the entire crotch region is elastic longitudinally of the article and therefore it is certainly possible to press the liquid-absorbent pad lying in the crotch region against the wearer's body zone including the urethral meatus vertically or obliquely from below. However, the entire crotch region pressed against the wearer's body may cause a problem of stuffiness. In addition, a relatively expensive elastic sheet must be used in the crotch region. Therefore, such article is not advantageous with respect also to its manufacturing cost.

SUMMARY OF THE INVENTION

In view of the problem as has been described above, it is an object of the present invention to provide a disposable a diaper which measures a liquid-absorbent pad to be tightly placed against a wearer's urethral meatus and an area in the vicinity thereof without an apprehension that the diaper may cause a significant stuffiness.

According to the present invention, there is provided a disposable diaper comprising a pants-type outer cover having a front waist region, a rear waist region, a crotch region therebetween, a waist-opening and a pair of leg-openings; and a liquid-absorbent pad attached to an inner surface of the outer cover and extending across the crotch region into the front and rear waist regions, wherein:

the outer cover is provided in a transversely middle of the front waist region with a zone defined to cover a wearer's urethral meatus and an area in the vicinity thereof and being elastic transversely of the diaper under effect of elastic members; the pad comprises a liquid-pervious topsheet, a liquid-impervious backsheet and a liquid-absorbent core wherein the pad has longitudinally opposite ends which extend transversely of the diaper and transversely opposite side edges which extend longitudinally of the diaper; an outer surface of the longitudinally opposite ends are joined to the inner surface of the outer cover; and outer surfaces of the side edges are joined to the inner surface of the outer cover along zones of the outer cover transversely spaced apart from each other across the transversely elastic middle zone.

According to a preferred embodiment of the present invention, the liquid-absorbent core of the pad member is formed on its outer surface along its transversely middle line with a groove extending longitudinally of the diaper so that the core may be easily bent along the groove.

According to another preferred embodiment of the present invention, the pad is formed along its transversely opposite side edges with a pair of barrier cuffs extending longitudinally of the diaper and adapted to be risable on the inner surface of the pad so that the pair of barrier cuffs cooperate with the inner surface of the pad to form a pair of channels adapted to be opened inwardly of the pad.

BRIEF DESCRIPTION OF THE DRAWINGS

FIG. 4 is a fragmentary sectional view taken along line IV—IV in FIG. 2.

DETAILED DESCRIPTION OF THE PREFERRED EMBODIMENTS

Details of a disposable diaper according to the present invention will be more fully understood from the description given hereunder with reference to the accompanying drawings.

Figure 1:
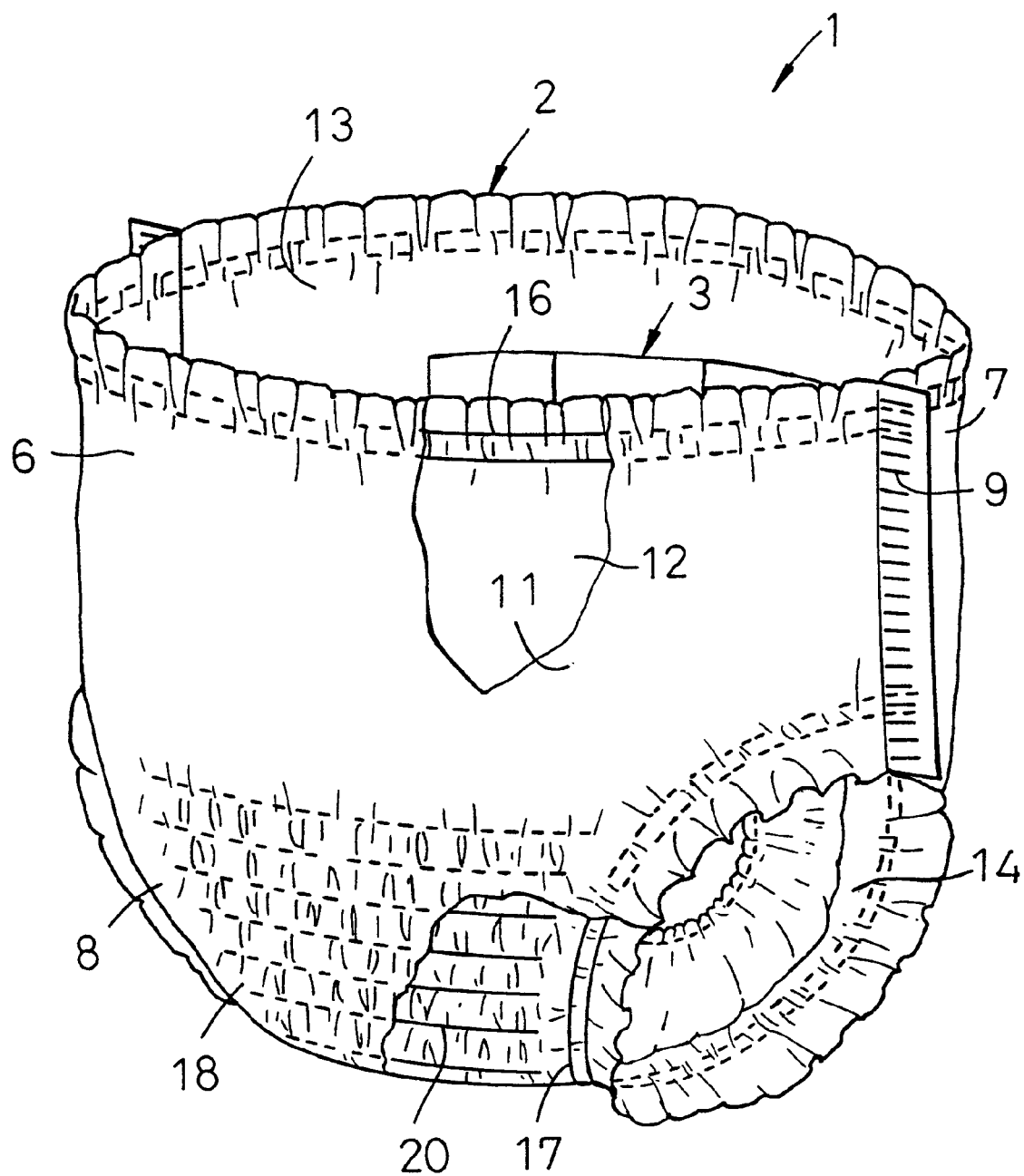
FIG. 1 is a perspective view of a disposable diaper according to the present invention having portions cutaway.

A pants-type or pull-on type disposable diaper 1 shown by FIG. 1 in a perspective view having portions cutaway comprises a pants-type outer cover 2 and a liquid-absorbent pad 3 attached to an inner surface of the outer cover 2.

The outer cover 2 comprises outer and inner sheets 11, 12 which are identical to each other in shape as well as in size and placed upon each other and bonded together. Configurationally, the outer cover member 2 has longitudinally a front waist region 6, a rear waist region 7 and a crotch region 8 extending between these two waist regions 6, 7. The front and rear waist regions 6, 7 have their transversely opposite side edges placed flat upon each other and joined together at spots 9 intermittently arranged in a vertical direction of the diaper along the side edges to form a waist-opening 13 and a pair of leg-openings 14. Along peripheries of the openings 13, 14, elastic members 16, 17 circumferentially extend, respectively, and are bonded under appropriate tension to an inner surface of at least one of the outer and inner sheets 11, 12 placed upon each other. The front waist region 6 and/or the crotch region 8 of the outer cover 2 include a zone 18 intended to cover the wearer's urethral meatus and an area in the vicinity thereof. In this zone 18, elastic members 20 are disposed between the outer and inner sheets 11, 12 so as to extend transversely of the outer cover 2 and secured under appropriate tension to the inner surface of at least one of the outer and inner sheets 11, 12. In general, the outer and inner sheets 11, 12 are made of a nonwoven fabric or a plastic film and preferably the outer sheet 11 is made of a breathable but liquid-impervious plastic film while the inner sheet 12 is made of a breathable nonwoven fabric offering a soft touch. It should be understood that the outer cover 2 is not limited to such two-layered construction and may be formed by only one of these two sheets 11, 12. No matter whether the outer cover 2 is formed by the sheet 11 or the sheet 12, the elastic members are preferably laid on the inner side of the sheet.

Figure 2:
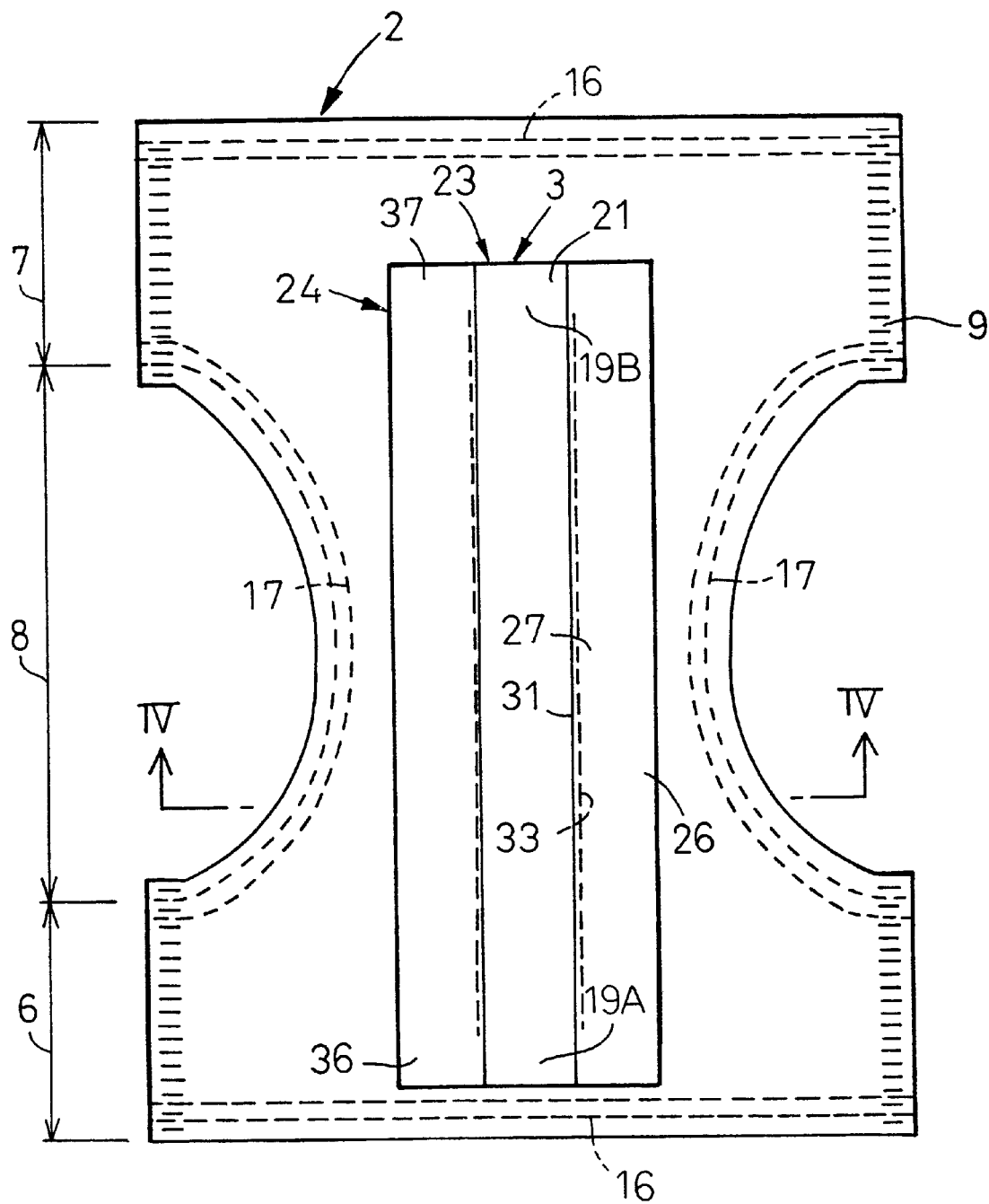
FIG. 2 is a plan view of the diaper of FIG. 1 in a developed state.
Figure 3:
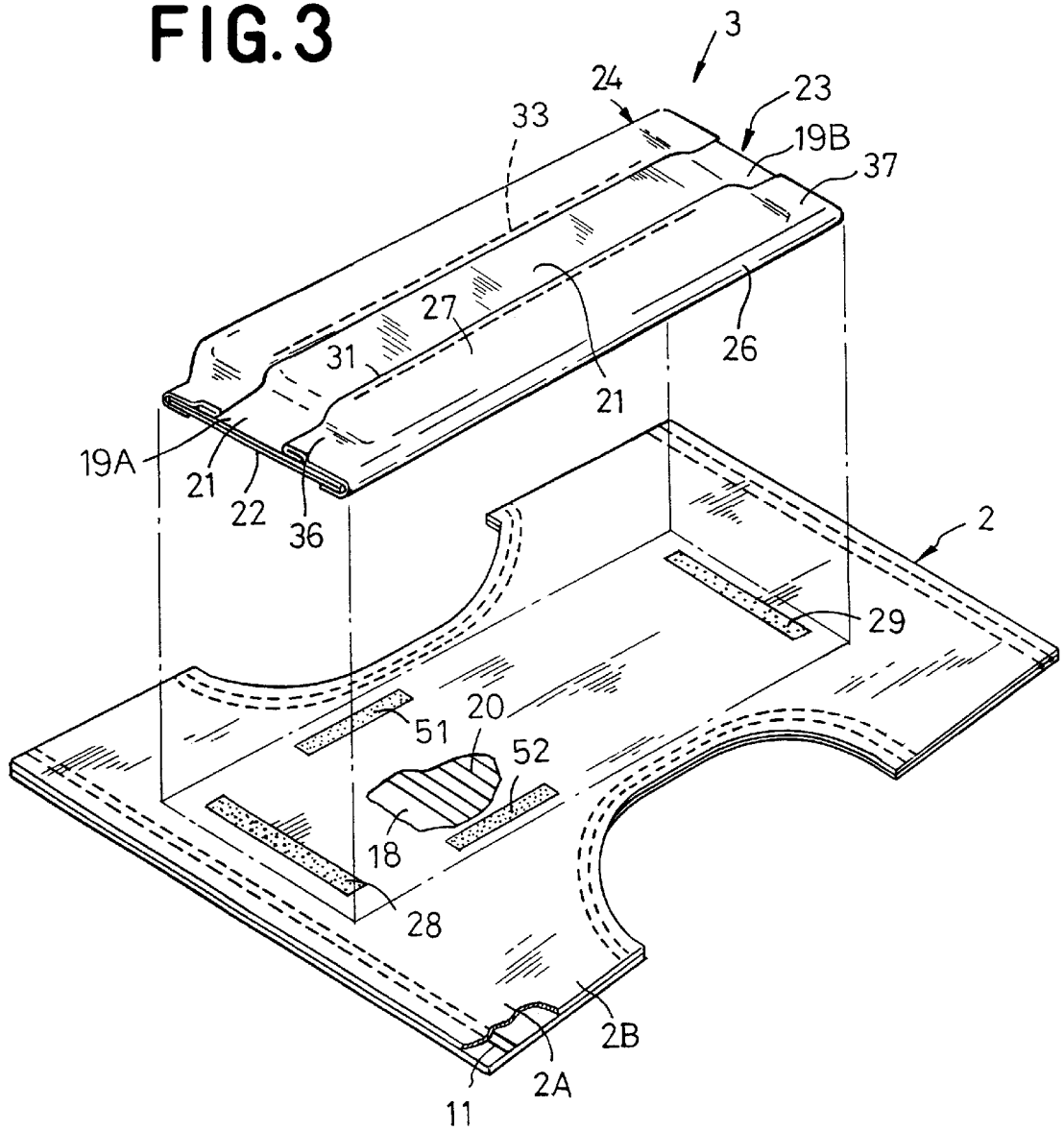
FIG. 3 is an exploded perspective view of the diaper of FIG. 2.

FIG. 2 is a plan view of the diaper of FIG. 1 in a state which is developed longitudinally as well as transversely after the front and rear waist regions of the diaper were separated from each other along the transversely opposite side edges thereof and FIG. 3 is an exploded perspective view of the diaper of FIG. 2. The liquid-absorbent pad 3 lies inside the outer cover 2 and extends across the crotch region 8 into the front and rear waist regions 6, 7. An outer surface of the pad 3 is joined at its longitudinally opposite ends 19A, 19B to the inner surface of the outer cover 2 along zones 28, 29 defined on the inner surface of the front and rear waist regions 6, 7, respectively, by means of hot melt adhesive (See FIG. 3). Additionally, the outer surface of the liquid-absorbent pad 3 is joined partially along its transversely opposite side edges to the inner surface of the outer cover 2 along two zones 51, 52 defined on the outer cover 2 so as to be transversely spaced apart from each other across the zone 18 by means of hot melt adhesive 55 as will be described later.

At The liquid-absorbent pad 3 comprises a pad body 23 having its top surface covered with a liquid-pervious topsheet 21 and its bottom surface covered with a liquid-impervious backsheet 22, and a pair of barrier cuffs 24 longitudinally extending along transversely opposite side edges of the pad body 23. As shown, each of the barrier cuffs 24 has a proximal edge zone 26 joined to the pad body 23 and a distal edge 27 extending in parallel to the proximal edge 26. The barrier cuff 24 pivotally collapses inwards around the proximal edge 26 so that the distal edge zone 27 may partially cover a top surface of the pad body 23. In this state, the inner surface of the distal edge 27 is bonded at longitudinally opposite ends 36, 37 to the topsheet 21. The barrier cuff 24 has an elastic member 33 secured under tension thereto along a ridge 31 of the distal edge 27.

FIG. 4 is a framentary sectional view taken along line IV—IV in FIG. 2, showing the diaper 1 slightly curved in its longitudinal direction with the liquid-absorbent pad 3 inside and the barrier cuffs 24 risen up under contractile effect of the elastic members 33. The pad body 23 is secured by contracts to form a plurality of gathers 25 as the elastic members 20 contract. In the vicinity of the zone 18 the pad body 23 is curved convexly towards the wearer's urethral meatus (not shown) and the area is the vicinity thereof.

The pad body 23 has a liquid-absorber 41 between the topsheet 21 and the backsheet 22 which extend outwards beyond a periphery of the core 41 and are placed upon each other and bonded together along their respective extensions. The core 41 comprises fluff pulp or a mixture of fluff pulp and superabsorptive polymer particles covered with a tissue paper (not shown). In order to facilitate the pad body 23 to be curved upwards as shown, a bottom surface of the core 41 is formed in its transversely middle with a groove 50 extending longitudinally of the core 41.

The pair of barrier cuffs 24 cooperate with the pad body 23 to form a pair of channels 48 adapted to be fully opened as the respective distal edge zones 27 rise up on the topsheet 21.

The present invention can be exploited not only in the form of the pants-type diaper as shown but also in the form of an open-type diaper. To bond the respective members together, a suitable adhesive agent such as hot melt adhesive or glue may be used and, for the heat-sealable members, the heat-sealing technique also may be used.

With the diaper arranged as has been described hereinabove, the pad body can be curved upwards against the wearer's urethral meatus and the area in the vicinity thereof vertically or obliquely from below. In this way, the diaper according to the present invention enables a quantity of urine discharged thereon to be absorbed more rapidly and reliably than it is achieved by the diaper of prior art in which the liquid-absorbent pad is placed against the wearer's crotch relying merely upon a circumferential fitting of the diaper around the wearer's body. In the crotch region, the elasticity is locally limited and therefore an apprehension that the diaper might become stuffy is correspondingly alleviated in comparison with the diaper of prior art in which the entire crotch region is pressed against the wearer's crotch.

What is claimed is:

1. A disposable diaper comprising:
   a pants-shaped outer cover having a front waist region having an upper and a lower portion, a rear waist region and a crotch region extending between said front waist region and said rear waist region, said crotch region having a longitudinal central portion, said outer cover being provided in a transversely middle of said front waist region with a middle zone which covers a wearer's urethral meatus and a surrounding area thereof, said middle zone extending from the lower portion of said front waist region to the longitudinal central portion said crotch region and including elastic members which cause said middle zone to be elastic transversely of said diaper;
   a waist-opening;
   a pair of openings, said middle zone extending from one leg-opening of said pair of leg-openings to another leg-opening of said pair of leg-openings; and
   a liquid-absorbent pad attached to an inner surface of said outer cover and extending across said crotch region into said front and rear waist regions, said liquid-absorbent pad comprising:
   a liquid-pervious topsheet;
   a liquid-impervious backsheet;
   a liquid-absorbent core;
   longitudinally opposite ends which extend transversely of said diaper; and
   transversely opposite side edges which extend longitudinally of said diaper,
   an outer surface of said longitudinally opposite ends being joined to the inner surface of said outer cover, and outer surfaces of said side edges being joined to the inner surface of said outer cover along zones of said outer cover which zones are transversely spaced apart from each other across said middle zone.

2. The diaper according to claim 1, wherein the liquid-absorbent core of said liquid-absorbent pad is formed on the outer surface thereof along the transversely middle thereof with a groove extending longitudinally of said diaper, along which groove said core may be easily bent.

3. The diaper according to claim 1, wherein said liquid-absorbent pad is formed along transversely opposite side edges thereof with a pair of barrier cuffs which extend longitudinally of said diaper, said pair of barrier cuffs configured to cooperate with said inner surface of said liquid-absorbent pad to form a pair of channels adapted to be opened inwardly of said liquid-absorbent pad.

* * * * *